US00PP34871P2

(12) United States Plant Patent
Doyle

(10) Patent No.: US PP34,871 P2
(45) Date of Patent: Dec. 27, 2022

(54) FIG TREE NAMED 'S-54'

(50) Latin Name: *Ficus carica*
Varietal Denomination: S-54

(71) Applicant: James F. Doyle, Clovis, CA (US)

(72) Inventor: James F. Doyle, Clovis, CA (US)

( * ) Notice: Subject to any disclaimer, the term of this patent is extended or adjusted under 35 U.S.C. 154(b) by 0 days.

(21) Appl. No.: 17/803,397

(22) Filed: Jun. 21, 2022

(51) Int. Cl.
*A01H 5/08* (2018.01)
*A01H 6/00* (2018.01)

(52) U.S. Cl.
USPC ..... Plt./211

(58) Field of Classification Search
USPC ..... Plt./211
CPC ... A01H 5/08; A01H 5/00; A01H 5/02; A01H 6/00
See application file for complete search history.

*Primary Examiner* — June Hwu
(74) *Attorney, Agent, or Firm* — Michelle Bos Legal LLC

(57) ABSTRACT

The 'S-54' fig tree is a common-type fig tree, characterized by high vigor, precocious growth, and abundant production of large yellow to yellow-green figs. 'S-54' figs have a very small, closed eye that restricts the entrance of insects and spores that may cause internal decay or unwanted pollination. The skin of 'S-54' figs is moderately thick and durable, making the fruit well-suited for packing and shipping as a fresh market product. The fruit pulp is an attractive red color, has fine texture and is sweet and rich in flavor.

5 Drawing Sheets

Latin name: *Ficus carica.*
Variety denomination: 'S-54'.

BACKGROUND OF THE VARIETY

'S-54' is a new and distinct variety of fig tree, which originated from a controlled cross carried out by the inventor in 2010 near Roseville, Calif. Fruit of a 'Desert King' fig tree (not patented) was manually pollinated with pollen from fruit of a '91C' caprifig tree (not patented). The 'Desert King' fruit was covered with a cloth sleeve cage before and after manual pollination to prevent pollination from other sources. At fruit maturity in the fall of 2010, the manually pollinated fruit was harvested and the seed was cleaned, dried and stored. The seed was subsequently planted in small containers in the spring of 2011 at Roseville, Calif. The resulting seedlings were planted in a test location near Traver, Calif. in the fall of 2011 and numbered 'S-1' through 'S-98'. Seedling 'S-54' was observed to be extremely precocious, and was selected for further evaluation after producing a first fig crop in August of 2012.

Asexual propagation of the 'S-54' fig tree was first carried out in 2016 near Wilton, Calif. by grafting on an existing three-year-old fig tree. The grafted 'S-54' tree produced and matured its first fruit in the summer of 2017. The fruit, leaves and branches were identical to those of the original 'S-54' seedling. The 'S-54' fig tree has since been reproduced over successive asexually propagated generations and has been observed to remain true to type and retain its distinctive characteristics.

BRIEF DESCRIPTION OF THE VARIETY

The 'S-54' fig tree bears large yellow- to yellow-green-skinned common figs, which do not require caprification (pollination) in order to set and mature fruit. The 'S-54' fig tree is characterized by high vigor, and is precocious, productive and a regular bearer. The tree produces two crops: a first "breba" crop, and a second, more productive "main" crop. The fruit eye of the S-54 is very small in size, thereby restricting entrance of many insects and spores that could otherwise enter the fruit and cause internal decay. The fruit skin is moderately thick and durable, making the fruit very suitable for packing and shipping as a fresh market product. The fruit pulp is an attractive red color, has fine texture and is sweet and rich in flavor. The fruit appears to hold its size later into the season than other commercial varieties of figs, thus extending the season for good size and quality fresh figs.

The 'S-54' fig tree can be distinguished from female parent 'Desert King', and from 'CA Brown Turkey' (not patented) and 'Calimyrna' (not patented), both which make up the genetic background of the male parent '91C', as shown in the following tables:

TABLE 1

Comparison of 'S-54' Fig Tree to 'Desert King' Fig Tree

| Characteristic | 'S-54' | 'Desert King' |
|---|---|---|
| Fig type | Common | San Pedro |
| Size of eye (main crop) | Small, closed | Medium, open |
| Pulp color | Deep red (greyed-purple 185A) | Amber to moderate red |

TABLE 2

Comparison of 'S-54' Fig Tree to 'CA Brown Turkey' Fig Tree

| Characteristic | 'S-54' | 'CA Brown Turkey' |
|---|---|---|
| Fig type | Common | Common |
| Skin color | Yellow to yellow-green | Purple |
| Pulp cavity | Filled | Often hollow |
| Size of eye | Small, closed | Medium |

TABLE 3

Comparison of 'S-54' Fig Tree to 'Calimyrna' Fig Tree

| Characteristic | 'S-54' | 'Calimyrna' |
|---|---|---|
| Fig type | Common | Smyrna |
| Size of eye | Small, closed | Large, open |

BRIEF DESCRIPTION OF THE PHOTOGRAPHS

DETAILED BOTANICAL DESCRIPTION OF THE VARIETY

Figure 1:
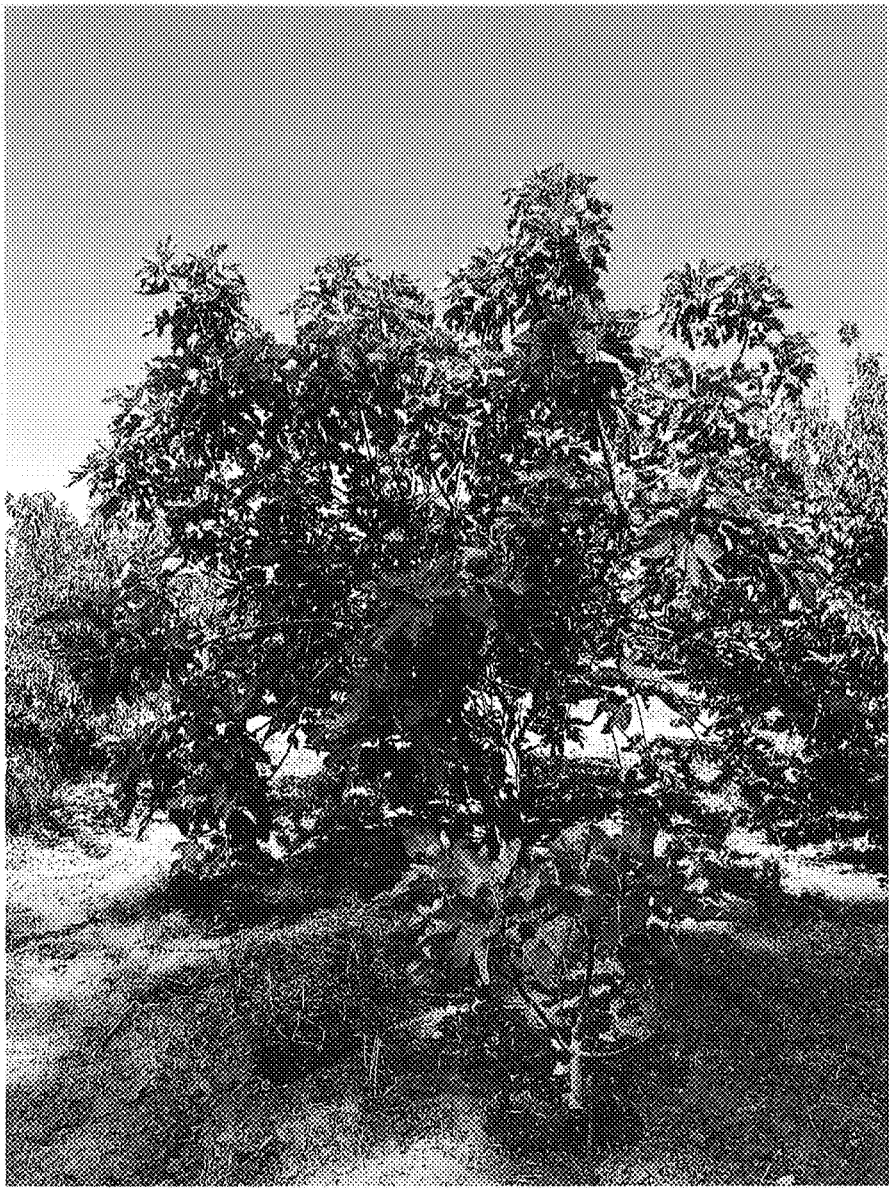
FIG. 1 depicts a 5-year-old 'S-54' fig tree growing near Sanger, Calif. (photo taken in 2022)
Figure 2:
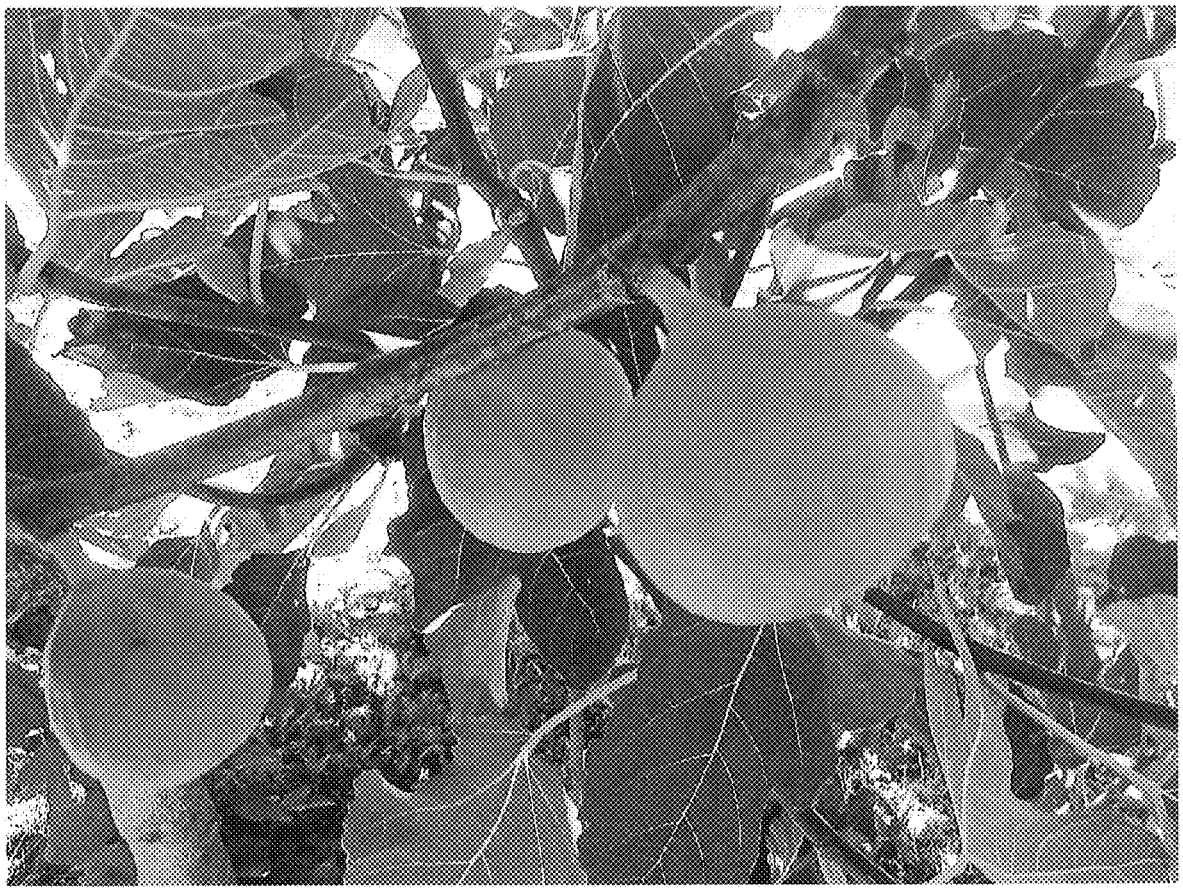
FIG. 2 depicts fruit and leaves on a 2-year-old 'S-54' fig tree growing near Wilton, Calif. (photo taken in 2018)
Figure 3:
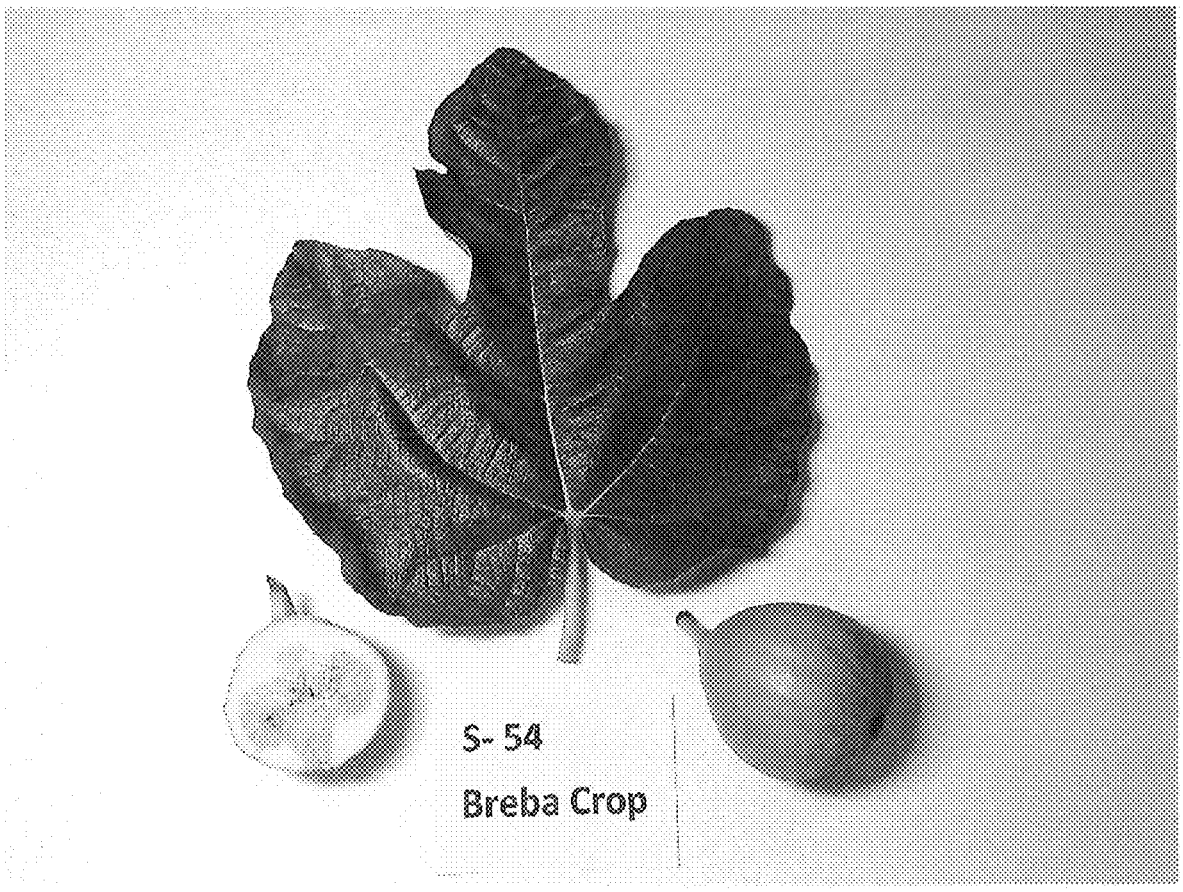
FIG. 3 depicts whole and sectioned fruit and a leaf from the 2021 breba crop of an 'S-54' fig tree growing near Sanger, Calif.
Figure 4:
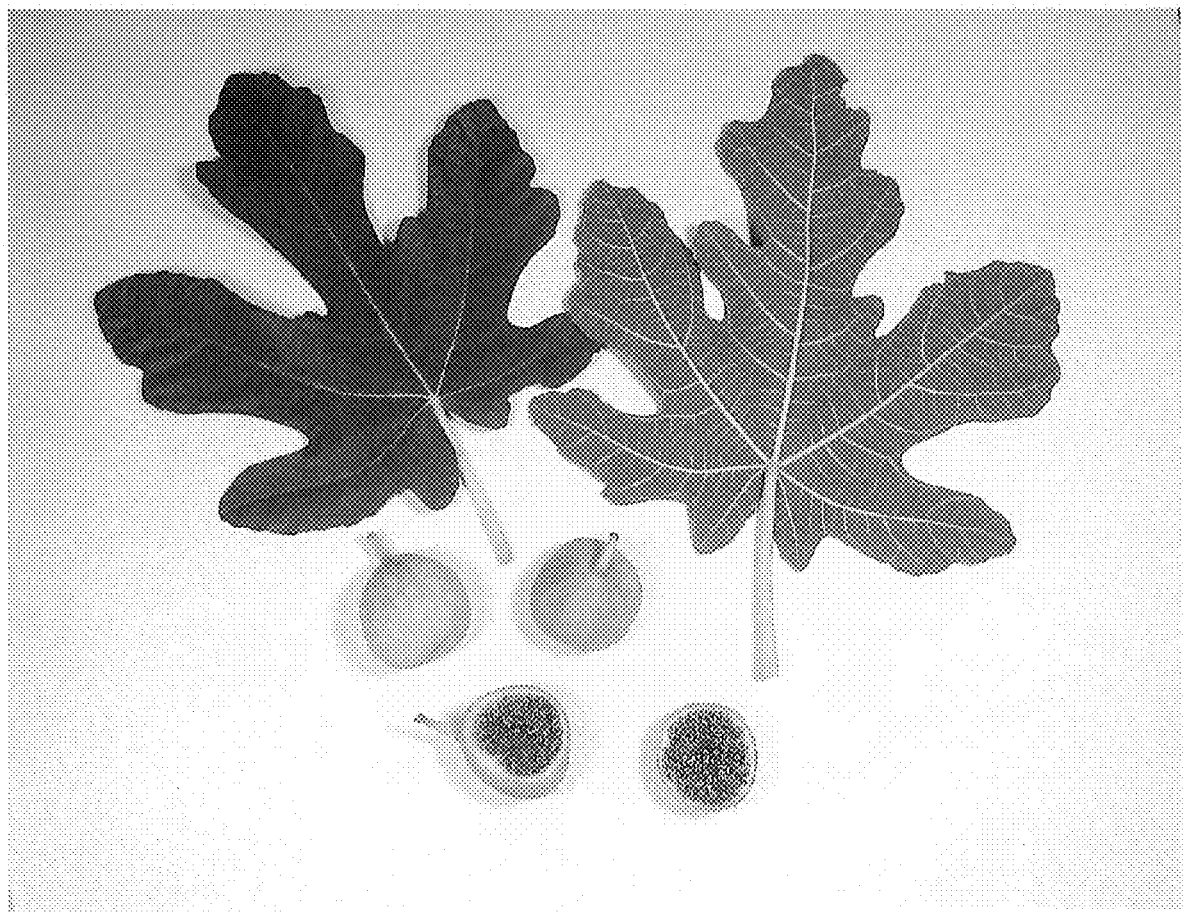
FIG. 4 depicts whole and sectioned fruit and leaves from the 2021 main crop of an 'S-54' fig tree growing near Sanger, Calif.
Figure 5:
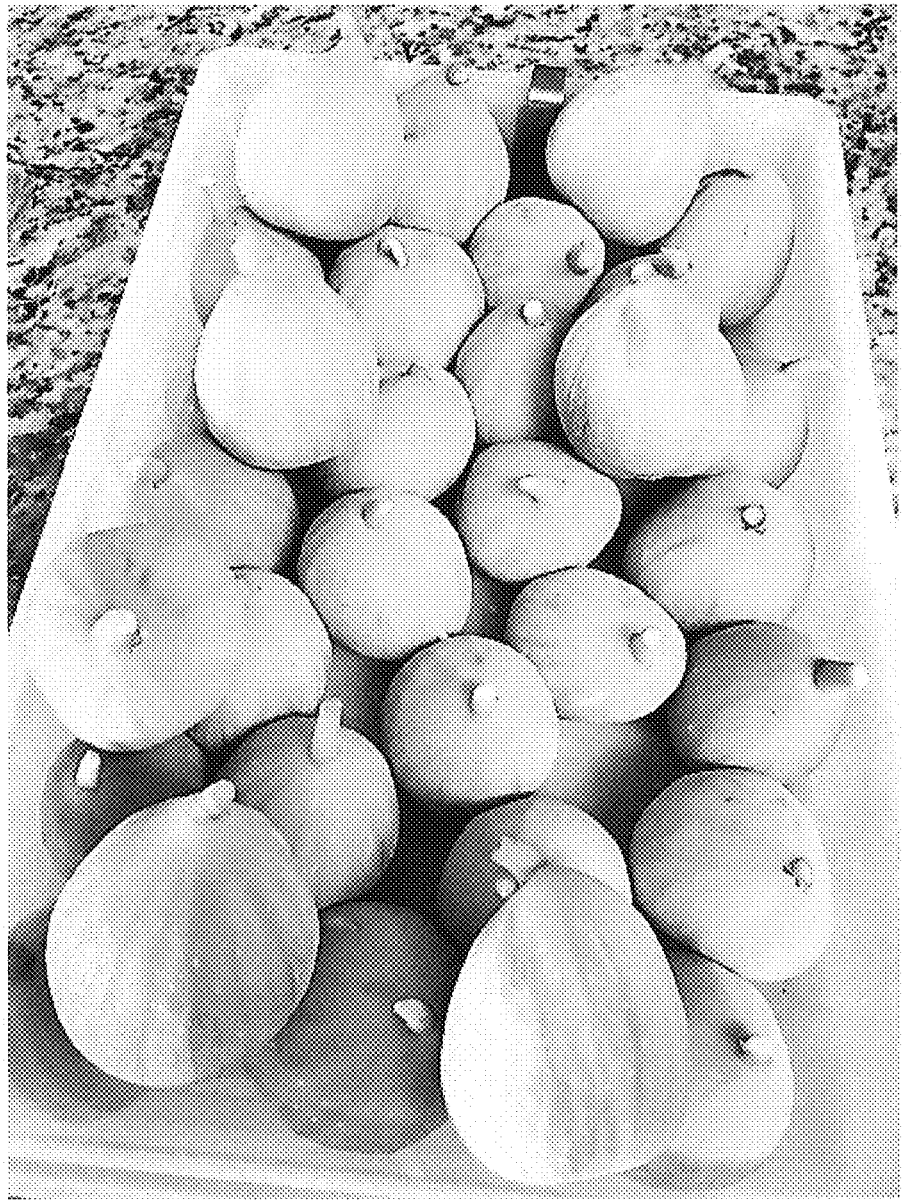
FIG. 5 depicts fruit from the 2021 main crop of an 'S-54' fig tree growing near Sanger, Calif.

The following-detailed botanical description is based on observations made primarily during the 2020 and 2021 growing seasons at Sanger, Calif. of trees planted in 2018. All colors are described according to The R.H.S. Colour Chart (Royal Horticultural Society, 3$^{rd}$ ed. 1995). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Form*.—Upright.

*Habit*.—Spreading.

*Vigor*.—Vigorous.

*Height*.—4.1 m.

*Spread*.—3.8 m to 5.2 m.

*Trunk diameter*.—21 cm at 10 cm above ground level.

*Bark texture*.—Relatively smooth with low, relatively fine vertical striations and numerous scattered lenticels.

*Bark color*.—Grey 201C with greyed-orange 177B vertical striations.

*Plant hardiness*.—'S-54' has been grown successfully in USDA Plant Hardiness Zones 7, 8 and 9, and can likely be grown in other zones as well.

Scaffold branches:

*Quantity*.—4, positioned 20 cm to 40 cm above ground level.

*Diameter*.—8 cm to 13 cm near trunk.

*Bark texture*.—Similar to trunk, with roughened longitudinal striations and scattered lenticels.

*Bark color*.—Grey 201C.

Secondary branches:

*Density of branching*.—Dense.

*Diameter*.—Varies widely; stronger secondary branches range from <1.4 cm to 5.4 cm.

*Color*.—Mature basal portions grey 201C; less mature tips grey 201A.

*Nodal swellings*.—Present near leaf scar; not prominent on young tree but expected to become more prominent as tree ages.

Shoots:

*Texture*.—Scattered short, stiff pubescence.

*Presence of weeping shoots*.—Weeping secondary shoots present, especially noticeable on lower portion of tree.

*Color*.—Yellow-green 144A.

*Tip bud shape*.—Conic with attenuate tip.

*Tip bud position*.—Variable, often moderately oblique to branch end.

*Tip bud color*.—Yellow-green 145A.

*Tip bud length*.—1.9 cm.

*Tip bud diameter*.—0.9 cm.

*Internodes*.—Quantity varies, from 10 to 19 internodes on shorter shoots, to 25 to 27 internodes on longer shoots; shortened internode length occurs near tip of shoot.

*Timing of terminal bud burst*.—Varies depending on the temperature of the growing location; usually between the last week of February and the second week of March in the Central Valley of California.

*Shape of two-year-old shoot*.—Straight.

Bark tubers:

*Location*.—Moderate number present on scaffolds from about 80 cm to 180 cm above ground level.

*Shape*.—Globose to oval.

*Relative size*.—Small, expected to increase in size as tree ages.

*Length*.—0.4 cm to 0.6 cm.

*Diameter*.—0.4 cm to 0.7 cm.

*Color*.—Gray 201C.

Leaves:

*Leaf form*.—Palmately lobed; usually five lobes, three lobes not uncommon.

*Lobe form*.—Latate.

*Central lobe form*.—Latate.

*Basal lateral lobes*.—Present.

*Base form*.—Calcarate.

*Sinus*.—Moderately deep; sinus bottoms variable in form, most frequently with upper sinus bottoms double "U" in form and lower sinus bottoms single "U" in form.

*Surface texture*.—Both surfaces pubescent; pubescence on upper surface short and stiff, pubescence on lower surface longer, relatively softer and more flexible; pubescence density greater along the leaf veins on both surfaces.

*Vein prominence*.—Very prominent on lower surface, less prominent on upper surface.

*Margin*.—Outer margins coarsely crenate with broad crenations; sinus margins entire.

*Length*.—18.5 cm to 22.0 cm.

*Width*.—19.0 cm to 24.0 cm.

*Upper surface color*.—Yellow-green 147A with yellow-green 150C veins.

*Lower surface color*.—Yellow-green 147B with yellow-green 150C veins.

Petiole:

*Length*.—Medium, 6.5 cm to 9.21 cm.

*Diameter*.—6.0 mm to 7.0 mm.

*Pubescence*.—Pubescent, with hairs denser and longer at petiole base.

*Color*.—Yellow-green 150D to yellow-green 154D near base.

Fruit:

Breba crop:

*Harvest maturity*.—Dependent on weather conditions, usually mid-June.

*Relative size*.—Large.

*Length*.—45 mm to 55 mm.

*Diameter*.—45 mm to 53 mm.

*Weight*.—43 g to 70 g.

*Form*.—Turbinate.

*Neck*.—Absent.

*Stem length*.—Short, 9 mm to 15 mm, slightly curved.

*Stem diameter*.—Thick, 5 mm to 6 mm.

*Stem pubescence*.—Many short fine hairs present, more dense at base of stem.

*Stem color*.—Yellow-green 151A to yellow-green 151C.

*Strength of attachment of stem to fruit*.—Strong.

*Bracts*.—Usually 3 irregular-shaped bracts at base of stem, appressed to upper shoulder of fruit; 2.0 mm to 3.0 mm long, 4.0 mm to 6.0 mm wide.

*Ribbing*.—Low longitudinal ribbing present; smooth, not prominent; yellow-green 153D.

*Eye*.—Small and tight, diameter 0.2 mm to 2.0 mm; numerous scales present around perimeter deter entrance of insects.

*Skin texture*.—Average thickness; durable; moderately glossy; fine, short pubescence present; surface checking and skin tears not usually present, longitudinal tears occasionally appear.

*Skin color*.—Predominant color ranges from yellow 11A to yellow-green 153C to yellow-green 153D; lighter-colored yellow-green 150D lenticels distributed over surface and concentrated on shoulders.

*Meat*.—Moderately thin near equator, 3.0 mm to 5.0 mm in thickness; thicker near basal and apical ends, 6.0 mm to 9.0 mm; tender texture; sweet flavor; white 155B.

*Pulp*.—Nearly always fills center of fruit; color varies from red 39B to orange-red 35A; soft, fine-grained texture.

*Seeds*.—Abundant; 1.25 mm diameter; oval; greyed orange 164C.

*Flavor*.—Sweet; rich; well-balanced.

*Number of abnormal fruits*.—Few.

Fruit:

Main crop:

*Harvest maturity*.—Dependent on weather conditions, usually starting in mid-July and extending until late fall.

*Relative size*.—Medium to large.

*Length*.—39 mm to 46 mm.

*Diameter*.—40 mm to 45 mm.

*Weight*.—34 g to 48 g.

*Form*.—Usually turbinate, occasionally spherical.

*Neck*.—Usually absent.

*Stem length*.—Medium, 16 mm to 20 mm, moderately curved.

*Stem diameter*.—Moderately thick, 4 mm to 6 mm.

*Stem pubescence*.—Many short fine hairs present.

*Stem color*.—Yellow-green 145B to yellow-green 151C.

*Strength of attachment of stem to fruit*.—Strong.

*Bracts*.—Usually 3 conic-shaped bracts at base of stem.

*Ribbing*.—Low longitudinal ribbing present; smooth, not prominent; yellow-green 144A to yellow-green 151A, usually darker than overall skin color.

*Eye*.—Very small diameter 0.0 mm to 1.0 mm; numerous small scales present around perimeter deter entrance of insects; yellow-green 145B.

*Skin texture*.—Moderately thick; fine, short pubescence; durable, skin tears not usually present, but occasionally appear longitudinally.

*Skin color*.—Predominant color ranges from yellow-green 144C to yellow-green 151A; very light bloom present; lighter-colored (yellow-green 150D) lenticels distributed over surface, more abundant from equator toward apex; lenticel size 1.0 mm to 2.0 mm diameter; lenticel color yellow-white 158B to yellow-green 150C.

*Meat*.—Medium thickness 2.5 mm to 4.0 mm along lateral surface; thicker near apex, 3.0 mm to 5.0 mm; firm texture; sweet flavor; white 155A.

*Pulp*.—Nearly always fills center of fruit; Greyed-purple 185A, becoming darker at full maturity; soft, fine- grained with many fibrous filaments.

*Seeds*.—Abundant; 1.0 mm diameter; oval to ovate; greyed orange 164C.

*Flavor*.—Sweet with some acidity; well-balanced.

*Number of abnormal fruits*.—Few.

*Resistance/susceptibility to pests & diseases*.—Not observed to date.

Market use: Well-suited for fresh market.

I claim:

1. A new and distinct fig tree named 'S-54' substantially as described and illustrated herein.

* * * * *